US009776040B2

(12) United States Patent
Sedic (10) Patent No.: US 9,776,040 B2
(45) Date of Patent: Oct. 3, 2017

(54) EXERCISING KEGEL MUSCLES USING PREPROGRAMMED EXERCISE PROGRAMS

(71) Applicant: LELO Inc., San Jose, CA (US)

(72) Inventor: Filip Sedic, Shanghai (CN)

(73) Assignee: LELO Inc., San Jose, CA (US)

( * ) Notice: Subject to any disclaimer, the term of this patent is extended or adjusted under 35 U.S.C. 154(b) by 742 days.

(21) Appl. No.: 14/090,823

(22) Filed: Nov. 26, 2013

(65) Prior Publication Data

US 2014/0155225 A1   Jun. 5, 2014

Related U.S. Application Data

(60) Provisional application No. 61/732,184, filed on Nov. 30, 2012.

(51) Int. Cl.
*A63B 23/00* (2006.01)
*A61N 1/36* (2006.01)
(Continued)

(52) U.S. Cl.
CPC .......... *A63B 23/20* (2013.01); *A61N 1/36007* (2013.01); *A63B 24/0062* (2013.01); *A63B 24/0075* (2013.01); *A63B 24/0087* (2013.01); *A61H 19/40* (2013.01); *A61H 23/0263* (2013.01); *A61H 2201/0153* (2013.01); *A61H 2201/5012* (2013.01); *A61H 2201/5061* (2013.01); *A61H 2201/5097* (2013.01); *A61H 2230/505* (2013.01); *A61H 2230/655* (2013.01); *A63B 2024/0093* (2013.01);
(Continued)

(58) Field of Classification Search
CPC . A63B 23/20; A63B 24/0062; A63B 24/0075; A63B 24/0087; A63B 2230/60; A63B 2071/0655; A63B 2024/0093; A63B 2225/20; A63B 2225/50; A61N 1/36007; A61H 2201/0153; A61H 2201/5061; A61H 19/40; A61H 23/0263; A61H 2230/655; A61H 2201/5097; A61H 2201/5012; A61H 2230/505
See application file for complete search history.

(56) References Cited

U.S. PATENT DOCUMENTS

2,541,520 A * 2/1951 Kegel .................... A61B 5/202
                                                        600/591
3,726,273 A * 4/1973 Cole ...................... A61B 5/227
                                                        482/112
(Continued)

*Primary Examiner* — Sundhara Ganesan
(74) *Attorney, Agent, or Firm* — Fenwick & West LLP (57) ABSTRACT

A Kegel muscle exercising apparatus includes various exercise programs that adaptively change depending on a user's exercise performance. This apparatus includes an insertable device for inserting into the body of a user, computer program code that contains exercise programs that specify operation of a stimulation mechanism by a controller, a stimulation mechanism that directs a user to contract her Kegel muscles according to an exercise program, a sensor that measures Kegel muscle contraction activity, and a controller that receives feedback from the sensor. This feedback comprises the results of an exercise program, and depending on the results, the apparatus can determine a different exercise program appropriate for the user. Following the different exercise programs allows a user to improve her Kegel muscle strength.

31 Claims, 3 Drawing Sheets

(51) Int. Cl.
*A63B 24/00* (2006.01)
*A63B 23/20* (2006.01)
*A63B 71/06* (2006.01)
*A61H 19/00* (2006.01)
*A61H 23/02* (2006.01)

(52) U.S. Cl.
CPC ... *A63B 2071/0655* (2013.01); *A63B 2225/20* (2013.01); *A63B 2225/50* (2013.01); *A63B 2230/60* (2013.01)

(56) References Cited

U.S. PATENT DOCUMENTS

| | | | | |
|---|---|---|---|---|
| 4,167,938 A * | 9/1979 | Remih | A61B 5/227 | 482/113 |
| 4,476,880 A * | 10/1984 | Giem | A61B 5/036 | 600/591 |
| 4,515,167 A * | 5/1985 | Hochman | A61B 10/0012 | 600/549 |
| 4,909,263 A * | 3/1990 | Norris | A61N 1/0524 | 600/551 |
| 5,483,832 A * | 1/1996 | Pauser | A61B 5/227 | 600/591 |
| 5,674,238 A * | 10/1997 | Sample | A61B 5/202 | 600/591 |
| 5,733,230 A * | 3/1998 | Sawchuck | A63B 23/20 | 482/111 |
| 5,787,892 A * | 8/1998 | Dabney | A61B 5/42 | 600/591 |
| 5,860,940 A * | 1/1999 | Schonfeld | A61B 5/04882 | 600/587 |
| 5,881,731 A * | 3/1999 | Remes | A61N 1/0512 | 128/885 |
| 6,063,045 A * | 5/2000 | Wax | A61M 25/10 | 482/112 |
| 6,264,582 B1 * | 7/2001 | Remes | A63B 23/20 | 482/8 |
| 6,289,894 B1 * | 9/2001 | Remes | A61B 5/04882 | 128/885 |
| 6,436,029 B1 * | 8/2002 | Benderev | A61F 2/0009 | 128/885 |
| 6,579,266 B2 * | 6/2003 | Mosel | A61B 5/202 | 600/29 |
| 6,625,495 B1 * | 9/2003 | Alon | A61N 1/0512 | 600/325 |
| 8,360,954 B2 * | 1/2013 | Kim | | 482/113 |
| 2001/0051327 A1 * | 12/2001 | Hatano | A63B 23/20 | 434/262 |
| 2003/0087734 A1 * | 5/2003 | Kring | A63B 23/20 | 482/112 |
| 2003/0148864 A1 * | 8/2003 | Blackford | A63B 21/026 | 482/124 |
| 2003/0220589 A1 * | 11/2003 | Leivseth | A61B 5/227 | 600/591 |
| 2004/0082446 A1 * | 4/2004 | Miyamoto | A61H 19/44 | 482/112 |
| 2004/0267172 A1 * | 12/2004 | Liu | A61H 9/005 | 601/46 |
| 2005/0148447 A1 * | 7/2005 | Nady | A63B 23/20 | 482/121 |
| 2005/0228316 A1 * | 10/2005 | Morgenstern | A61B 5/04882 | 600/591 |
| 2006/0036188 A1 * | 2/2006 | Hoffman | A61B 5/0002 | 600/591 |
| 2007/0112284 A1 * | 5/2007 | Hoffman | A61B 5/0002 | 600/591 |
| 2007/0142191 A1 * | 6/2007 | Schuurmans Stekhoven | A63B 23/20 | 482/148 |
| 2007/0185417 A1 * | 8/2007 | Mittal | A61B 5/04882 | 600/591 |
| 2008/0139876 A1 * | 6/2008 | Kim | A61B 5/202 | 600/29 |
| 2009/0129205 A1 * | 5/2009 | Reichow | A63B 69/0053 | 368/9 |
| 2009/0270963 A1 * | 10/2009 | Pelger | A61B 5/04882 | 607/138 |
| 2010/0106216 A1 * | 4/2010 | Cha | A61N 1/0524 | 607/41 |
| 2010/0240495 A1 * | 9/2010 | Law | A63B 21/0004 | 482/9 |
| 2011/0092779 A1 * | 4/2011 | Chang | A61B 5/00 | 600/301 |
| 2012/0053017 A1 * | 3/2012 | Kushnir | A63B 21/00196 | 482/8 |
| 2012/0172679 A1 * | 7/2012 | Logan | A61B 5/082 | 600/301 |
| 2012/0183940 A1 * | 7/2012 | Aragones | G06F 19/3437 | 434/247 |
| 2013/0018308 A1 * | 1/2013 | Rao | A63B 23/20 | 604/99.04 |
| 2013/0130871 A1 * | 5/2013 | McCoy | A63B 23/20 | 482/113 |
| 2013/0324380 A1 * | 12/2013 | Horsley | A63B 23/20 | 482/131 |
| 2014/0066813 A1 * | 3/2014 | Daly | A63B 23/20 | 600/591 |
| 2014/0088471 A1 * | 3/2014 | Leivseth | A63B 23/20 | 601/89 |
| 2015/0273270 A1 * | 10/2015 | Brinkhaus | A63B 23/20 | 482/8 |

* cited by examiner

EXERCISING KEGEL MUSCLES USING PREPROGRAMMED EXERCISE PROGRAMS

BACKGROUND

The present invention relates generally to a Kegel exercising apparatus, and more particularly to an intelligent Kegel exercising apparatus that adaptively changes its exercise programs depending on a woman's exercise performance.

Urinary incontinence in women is a condition involving the involuntary leakage of urine. This condition is caused by the weakening of the pelvic muscles (also called the Kegel muscles) that aid in controlling urination. Urinary incontinence may be caused by neurological injury, birth defects, pregnancy and childbirth, or menopause, and is often diagnosed in women over age 60, as well as women struggling with problems such as obesity and diabetes.

To combat urinary incontinence, Kegel exercising methods have been developed to strengthen the Kegel muscles. These exercises serve to develop stronger reflexive contractions following a rise in intra-abdominal pressure. Kegel exercises have also been cited in strengthening pelvic muscles for easier pregnancy and childbirth, increasing pleasure during sexual activity, and treating conditions such as vaginosis. However, it can be difficult to perform these exercises because they are challenging and easily done incorrectly, and there is no effective way to measure exercise results and graduate to a more advanced exercise upon improvement.

Several devices have been invented to aid women in Kegel exercises. Some involve electrical stimulation of the Kegel muscles, and some require a user to manually use their hands to manipulate the device during exercise. A few devices provide air pressure gauges that measure muscle contraction strength. While using these devices may be more effective than trying to perform Kegel exercises alone, they are inconvenient and complicated, and there still does not exist a good method of improving the exercises, customizing the exercises to a specific user, or evaluating the exercise results. An easy-to-use device that overcomes these limitations is desirable.

SUMMARY

Embodiments include an intelligent Kegel exercising apparatus that can adaptively change its exercise programs depending on a woman's exercise performance, and embodiments include a method of exercising the Kegel muscles using the apparatus. In one embodiment, the Kegel exercising apparatus comprises a stimulation mechanism, a sensor, and a controller. Computer program code stored on a memory includes one or more exercise programs that specify operation of the stimulation mechanism by the controller. For example, the stimulation mechanism may provide a stimulus when a user is to contract her Kegel muscles. The sensor can measure these muscle contractions, and the controller may receive feedback from the sensor. In one embodiment, the feedback from the sensor comprises results of an exercise program.

Another embodiment is an intelligent Kegel exercising apparatus where the computer program code for analyzing the exercise program results also has the ability to automatically select the next exercise program based on the results. In another embodiment, a user can select the next exercise program on the apparatus.

A further embodiment includes an intelligent Kegel exercising apparatus that has an interface to an external device for sending the exercise program results to a user. As used herein, the term "external device" refers to a computer, a mobile device, a remote control, a docking station or base, or other devices that can connect to (wired or wirelessly) and/or communicate with the apparatus. For example, exercise program results may be sent through an interface to a computer of a medical specialist, who therefore may monitor a patient's progress as she improves her ability to contract the Kegel muscles. In another embodiment, an external device is used to manipulate the controller, where the external device communicates remotely with the controller.

An additional embodiment is a method for exercising the Kegel muscles. After the apparatus is inserted into a body of a user, an exercise program can be initiated. Then, after monitoring results of the exercise program, the user may select and initiate a second exercise program. In another embodiment, the apparatus automatically selects and initiates the second exercise program after monitoring the results of the first exercise program.

The features and advantages described in this summary and the following detailed description are not all-inclusive. Many additional features and advantages will be apparent to one of ordinary skill in the art in view of the drawings, specification, and claims hereof.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Figure 1A:
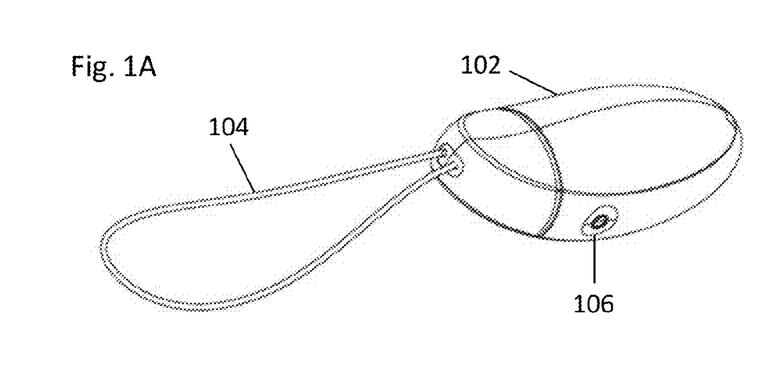
FIG. 1A is a diagram illustrating components of a Kegel muscle exercising apparatus, in accordance with an embodiment of the invention.

Referring first to FIG. 1A, there is shown a diagram illustrating components of a Kegel muscle exercising apparatus, in accordance with an embodiment of the invention. The embodiment of FIG. 1A illustrates the insertable device 102 of the apparatus, which is insertable into the body of a user. FIG. 1A shows the insertable device 102 as comprising the shape of a smooth oblong bead. Other embodiments of the insertable device 102 may comprise a round bead, a textured bead, or a device of a different shape or texture. The apparatus may further comprise an insertion and/or removal device, such as a string 104 connected to the bead, whereby the string 104 serves as a tool for efficient insertion and removal of the apparatus from a body. The apparatus also may comprise a control, such as a power button 106 or a power switch for turning power on and off, for changing settings of the apparatus, or for otherwise controlling the apparatus.

Figure 1B:
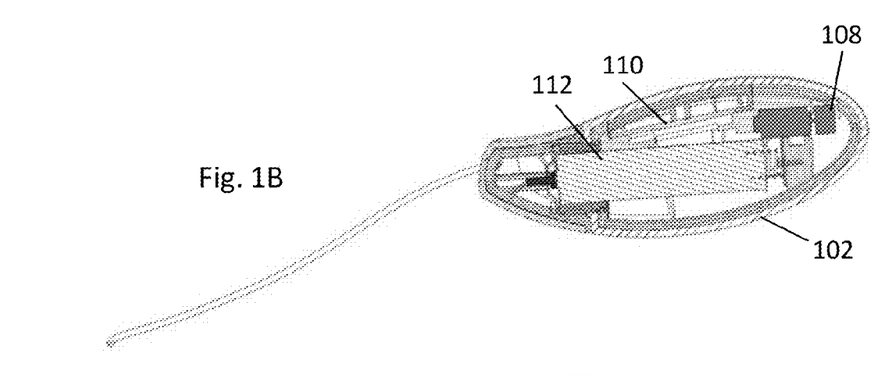
FIG. 1B is a diagram illustrating a lengthwise cross-sectional view of the inner components of a Kegel muscle exercising apparatus, in accordance with an embodiment of the invention.

FIG. 1B is a diagram illustrating a lengthwise cross-sectional view of the inner components of a Kegel muscle exercising apparatus, in accordance with an embodiment of the invention. Many components are located inside the insertable device 102, in this embodiment. For example, there is a stimulation mechanism 108 inside the device, though this mechanism can be otherwise integrated with the device, such as being in a component outside but attached to the insertable device 102. In one embodiment, the stimulation mechanism 108 comprises a motor for vibrating the apparatus, wherein the stimulus provided to the user is a movement of the device generated by the motor, such as a vibration of the device. In further embodiments, rather than having a motor (or in addition to the motor), the stimulation mechanism may comprise a vibrator, electromechanical device, an electromyography stimulation device (EMG device) or other mechanism for providing a stimulus. The stimulus itself may comprise a vibration, an electrical impulse, or another type of stimulus. In other embodiments, the device includes more than one stimulation mechanism, and these may be stimulation mechanisms of the same type or of different types.

The stimulation mechanism 108 acts to provide a stimulus, which may provide a pleasant sensation for a user and additionally may direct a user, who has inserted the insertable device into her body, to perform an action. This action comprises the contraction of Kegel muscles. Therefore, the stimulation mechanism 108 may direct exercise programs of the apparatus, where the stimulation mechanism 108 is activated at specific times to alert the user to contract her Kegel muscles, and whereby a particular pattern of stimulation may comprise an exercise program. For example, a first exercise program might begin with a one-second stimulus specifying to a user to contract her Kegel muscles for a ten-second period, after which there is another one-second stimulus specifying to a user to relax her Kegel muscles for another ten-second period. This contraction-relaxation pattern could repeat for ten cycles. In further embodiments, an exercise program might have a contraction period and/or relaxation period that lasts for five seconds, or for fifteen seconds, or for another period of time, or an exercise program may comprise a contraction-relaxation pattern that repeats for five cycles, or for fifteen cycles, or for another number of cycles.

Thus, different exercise programs may exhibit varying stimulation patterns. In one embodiment, a longer contraction period and shorter relaxation period comprises an exercise program for a user with relatively strong Kegel muscles. In another embodiment, a shorter contraction period and longer relaxation period comprises an exercise program for a user with relatively weak Kegel muscles.

Furthermore, different exercise programs might vary by stimulus strength or duration. For example, a strong stimulus might indicate an instruction for a strong muscle contraction, while a weak stimulus might indicate an instruction for a weak muscle contraction. Additionally, a strong stimulus might indicate that a user is performing an exercise program correctly, in response to a muscle contraction by a user, and a weak stimulus might indicate that a user is performing an exercise program incorrectly, in response to a muscle contraction by a user. In another embodiment, a longer stimulation time indicates an instruction for a longer muscle contraction, while a shorter stimulation time indicates an instruction for a shorter muscle contraction. In a further embodiment, the stimulation occurs stochastically.

In one embodiment, an exercise program comprises a number of short stimuli, where a short stimulus is provided, and the next short stimulus is provided as soon as a user completes a Kegel muscle contraction. This stimulation pattern might repeat a number of times, for example, thirty times. The reaction times of the muscle contractions by a user can be measured and analyzed by the apparatus to aid in determining a second appropriate exercise program for the user.

Another component located inside the device of the embodiment of FIG. 1 is the sensor 110. The sensor 110 can be located at various positions inside the device, on an outer surface of the device, or otherwise integrated on or within the device. The sensor 110 is generally configured to measure Kegel muscle contraction activity by a user. These measurements or the interpretation or analysis of these measurements comprise the results of each exercise program. In one embodiment, the sensor 110 comprises a pressure sensor that measures the pressure of Kegel muscle contractions. In another embodiment, the sensor comprises an electromyography or EMG signal sensor that measures the electrical activity produced by the Kegel muscles. The device can also have a variety of other sensors that take measurements or readings as the user is performing the exercise, such as a weight sensor, a temperature sensor, a biosensor, or any other type of sensor for collecting data for a user. The device may also include more than one sensor, and these may include sensors of the same type or of different types. In further embodiments, the sensor 110 performs a calibration after insertion of the insertable device into the body of a user, so that a standard can be set before measurements are made by the sensor 110.

In some embodiments, a rechargeable and/or replaceable power source 112 is coupled to apparatus, e.g., to the stimulation mechanism, to provide power to the apparatus. Examples of power sources include a battery, a solar-powered charger, or another power source. In other embodiments, the apparatus may be received by or docked into a base or docking station, whereby the base or docking station is electrically coupled to the apparatus for providing power to the apparatus or communicating with the apparatus. For example, the base or docking station can include a power connector to which apparatus connects to recharge the apparatus. As another example, the base or docking station may provide inductive charging to the apparatus. The apparatus can also be charged in other ways, such as by being connected by a power cord to the wall.

With regard to communicating with the apparatus, the docking station may receive information from or transmit information to the apparatus. As one example, the apparatus may download the results of the exercise programs to the docking station. Where the docking station is connected to a computer, this data may be provided to the computer and stored or sent across a network to another user (e.g., a doctor). In addition, data can be transmitted to the apparatus from the computer and possibly from another computer across a network (e.g., a doctor's computer). The data might include new or different exercise programs, changes to certain settings of the device, among other information. Some embodiments do not include a base or docking station, and the apparatus may be connected directly to the computer for communication or sharing of data.

Figure 1C:
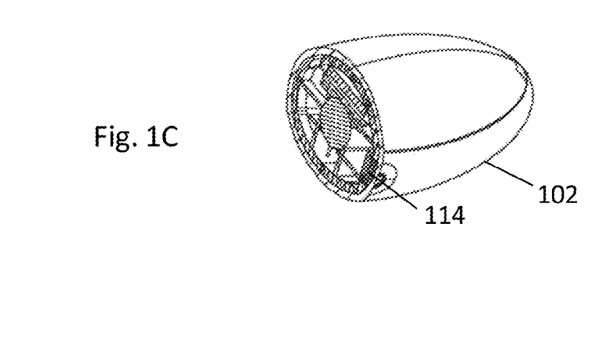
FIG. 1C is a diagram illustrating a widthwise cross-sectional view of the inner components of a Kegel muscle exercising apparatus, in accordance with an embodiment of the invention.

FIG. 1C is a diagram illustrating a cross-sectional view of the inner components of a Kegel muscle exercising apparatus, in accordance with an embodiment of the invention. In the embodiment of FIG. 1C, a controller 114 is visible. The controller 114 is integrated within the insertable device 102 and is coupled to the stimulation mechanism 108 and the sensor 110. The controller 114 may comprise a microprocessor, a processor, or it may comprise any other means of control.

The Kegel muscle exercising apparatus also comprises computer program code stored on a memory. This code includes one or more exercise programs, which specify operation of the stimulation mechanism 108 by the controller 114. Thus, the controller 114 directs the stimulation mechanism 108 to provide a stimulation pattern according to the exercise program that is currently running. A user then performs the exercise by contracting her Kegel muscles in response to the stimulation. The sensor 110 measures the Kegel muscle contractions of the user, and the controller 114 is configured to receive feedback from the sensor 110. This feedback provides information about how the user performed with regard to the exercise conducted, which can be used to determine a next exercise program that might be appropriate for the user. For example, a pressure sensor can be used to measure the amount of pressure applied by a user in contracting the Kegel muscles, and this feedback can be used to determine whether a more or less challenging exercise program is appropriate for the user. If the amount of pressure was lower (or higher), than a threshold pressure for the exercise program, the controller 114 can provide a less challenging (or more challenging) next program. In one embodiment, the controller 114 analyzes the average strength of the muscle contractions by a user during a first exercise program, and then selects a more challenging or less challenging second exercise program.

In another embodiment, the controller 114 analyzes the reaction times of the muscle contractions by a user in conjunction with other exercise program results, to select an appropriate next exercise program for the user. In an additional embodiment, when the controller 114 receives feedback from the sensor 110, if the feedback indicates that a user is performing the exercise correctly, the controller 110 directs the stimulation mechanism 108 to provide a stronger stimulus. In an additional embodiment, if the feedback indicates that a user is performing the exercise incorrectly, the controller 110 directs the stimulation mechanism 108 to provide a weaker stimulus.

Exercise programs can differ from one another in any way in terms of frequency, strength, duration, etc. of the stimuli (and thus resulting in different frequency, strength, duration of the muscle contractions). For example, a first exercise program might have 10 repetitions of a particular pattern, and a second exercise program might have 5 or 15 repetitions of the same pattern. As another example, a first exercise program might have 10 repetitions of a particular pattern, and a second exercise program might have 10 repetitions of a different pattern. As a further example, a first exercise program and second exercise program might be the same, but with a time interval in between for resting.

Figure 2:
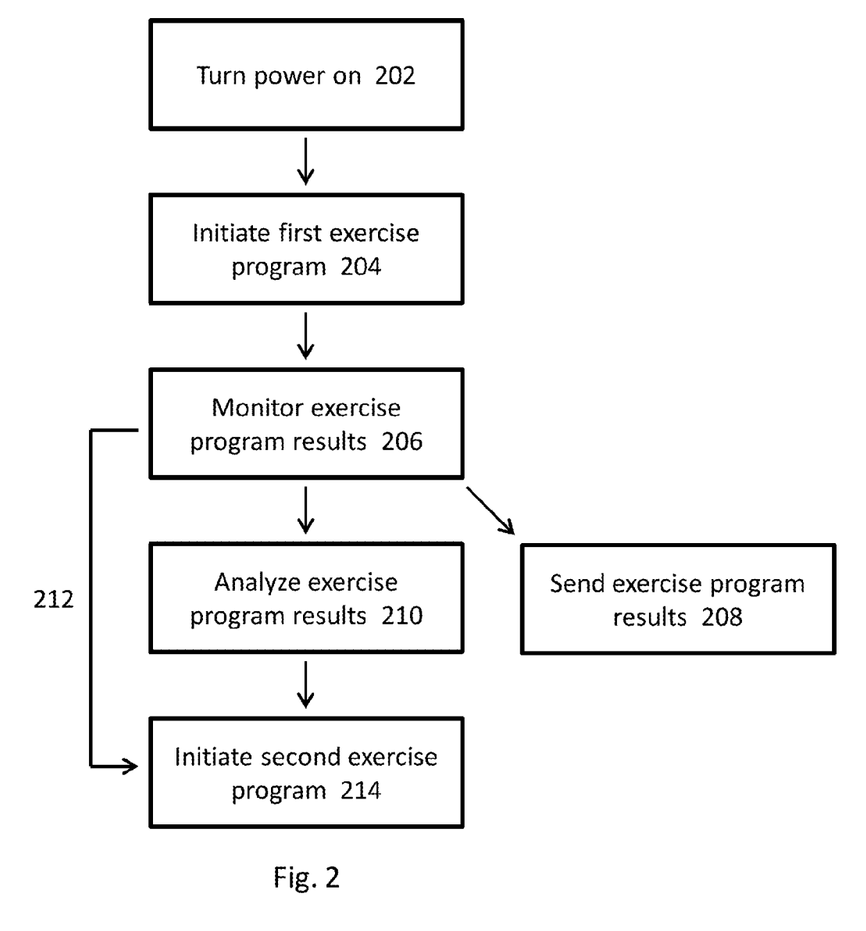
FIG. 2 is a block diagram of a process for initiating an exercise program, and, based on the exercise program results, initiating a second exercise program, in accordance with an embodiment of the invention.

Referring now to FIG. 2, there is shown a diagram illustrating the steps performed in a process for initiating an exercise program, and, based on the exercise program results, initiating a second exercise program, in accordance with an embodiment of the invention. It should be understood that these steps are illustrative only. Different embodiments may perform the illustrated steps in different orders, omit certain steps, and/or perform additional steps not shown in FIG. 2. The method can start and end at various points in the process, and typically is a continuous process with multiple steps occurring simultaneously, so FIG. 2 provides only an example of one ordering of method steps. In addition, the methods can be performed using another apparatus capable of performing the steps provided below.

FIG. 2 describes a method for exercising the Kegel muscles. One step includes powering on 202 of a Kegel muscle exercising apparatus (e.g., by a user manipulating a control on the apparatus or on an external device, or by an auto-power on that occurs by a sensor on the device detecting that the device has been inserted). An additional step includes initiating a first exercise program 204 on the apparatus. This can be performed by, for example, manipulating the controller to direct the stimulation device. In some embodiments, a user may initiate a first exercise program by interacting with the apparatus itself. For example, the user could interact with a control on the apparatus. In other embodiments, the first exercise program initiates upon insertion of the apparatus or a certain amount of time after the apparatus is powered on.

In other embodiments, a user may use an external device, such as a remote control, a mobile device, or a computer, to manipulate the apparatus or the controller within the apparatus to initiate a first exercise program. The external device communicates with the controller via an interface of the apparatus. The interface may comprise a wired interface, such as a cable coupled to the apparatus and to a computer or other external device. In some embodiments, the cable is a USB cable. The interface may alternatively comprise a wireless interface, such as a wireless transceiver that transmits and/or receives control signals between the apparatus and a computer, a remote control, a mobile device, or other external device. In some embodiments, the external device is connected to a network (e.g., the Internet, a cellular phone network, etc.) directly or via a computer or other device. In other embodiments, the external device communicates with or controls the apparatus via infrared, radio frequency, etc. Thus, the apparatus can be controlled via computer, phone, remote, etc. by the user with whom the apparatus is in contact or by another user using the computer, phone, remote, etc. There may also be more than one external device to control the apparatus. Since the apparatus is used inside the body, the external device provides a mechanism by which the user or another user can interact with and control the apparatus without having to remove the apparatus from the body.

A next step includes monitoring the results 206 of an exercise program. Exercise program results are measured by the sensor 110. In some embodiments, after one exercise program has been completed, a user may view the results of the exercise program on a display unit coupled to the apparatus. In one embodiment, there is a display unit within or on the apparatus on which to view the exercise program results. In another embodiment, the external device may have a user interface that displays information to the user. In this case, the exercise program results can be sent 208 to the external device via an interface of the apparatus. Where the external device is a remote control, it may have a screen or other display that provides exercise results or other data to the user. Where the external device is a computer, a software program may allow the user to interact with the device, view exercise results and other data, upload other exercise programs, modify existing programs, design a customized program, analyze result data, and so forth. The results can also be sent 208 directly across a network from the apparatus where the apparatus is capable of connecting to a network, or the results can be sent 208 to an external device that can then be used to send them across a network or to another device. In some embodiments, the results are analyzed before sending 208, and in other embodiments they are not. For example, the data collected about the exercises performed could be sent to a user's computer or a doctor's computer, and the analysis of the results performed there.

In addition to sending the exercise program results 208, in another step the exercise program results are analyzed 210 in accordance with instructions within computer program code in the apparatus. This analysis allows a second exercise program appropriate for the user to be selected. A user may then manually select a second exercise program to be initiated 214. In other embodiments, computer program code analyzes the exercise program results 210, and, based on the results, automatically determines a second exercise program appropriate for the user. In further embodiments, the program begins automatically 212 after the computer program determines a second exercise program. In this case, the next exercise program may begin without user interaction, but may simply be started by the apparatus upon completion of the prior exercise program or after a certain period of time. In some embodiments, the analysis 210 occurs before the automatic 212 starting of the next program. Though not illustrated in FIG. 2, the method steps can continue in the same manner with additional exercise programs being initiated over a period of time and results of those programs being monitored and analyzed.

Figure 3:
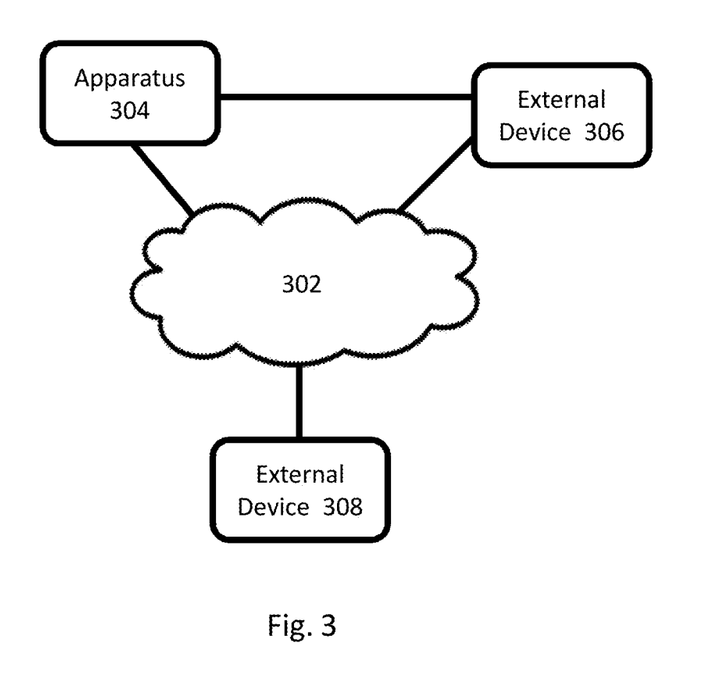
FIG. 3 is a network diagram of a system for providing exercise program results to a user, in accordance with an embodiment of the invention.

FIG. 3 is a network diagram of a system for providing exercise program results to a user, in accordance with an embodiment of the invention. After the results of the exercise program have been monitored 206 and collected, they can be sent 208 from the apparatus, including sending to a location via a network 302. In one embodiment, the exercise program results are sent from the Kegel muscle exercising apparatus 304 across the network 302. In another embodiment, the results are sent from the apparatus 304 to an external device 306 (for example, a computer, a remote control, a docking station or base, etc.) and sent from the external device 306 across the network 302 or sent from the external device 306 to a second external device 306, and then across the network (e.g., sent to a remote control and from the remote control to the user's computer). In both cases, the exercise program results can be sent across the network to another external device 308 (e.g., a doctor's computer, a friend's computer, etc.). In one example, the results can be sent to an external device 306 of a third party, which analyzes the results, and then sends the analysis and the results to another external device 308 (e.g., a doctor's computer, the user's computer, etc.).

The interface of the apparatus that allows the data to be sent from the apparatus may comprise a wired interface, such as a cable coupled to the apparatus 304 and to a computer 306, In some embodiments, the cable is a USB cable. The interface may alternatively comprise a wireless interface, such as a wireless transceiver that transmits and/or receives control signals between the apparatus 304 and an external device 306 or 308. In some embodiments, the interface is a radio-frequency (RF) transceiver for transmitting/receiving RF signals between the apparatus 304 and an external device 306. One example of an RF transceiver that could be used is a low power 2.4 GHz RF transceiver (e.g., transceiver CC2500 by TEXAS INSTRUMENTS®). In other embodiments, the interface uses other technology for transmitting/receiving signals between the apparatus 304 and external devices 306 and/or 308. For example, the interface can use BLUETOOTH®, WiFi, infrared, laser light, visible light, acoustic energy, among a variety of other ways to transmit information wirelessly between the apparatus 304 and external devices 306 and/or 308. The network 302 can be any type of network, such as the Internet, a local area network, wide area network, a cellular network, and so forth.

While various embodiments have been described above, it should be understood that they have been presented by way of example only, and not limitation. Thus, the breadth and scope of a preferred embodiment should not be limited by any of the above-described exemplary embodiments.

What is claimed is:

1. A Kegel muscle exercising apparatus comprising:
an insertable device;
a stimulation mechanism integrated within the insertable device, the stimulation mechanism configured to deliver one or more physical stimuli to a user at a location of the insertable device;
a controller integrated within the insertable device and coupled to the stimulation mechanism;
computer program code stored on a memory and including one or more exercise programs that specify operation of the stimulation mechanism by the controller, wherein the operation corresponds with an instruction specified by the exercise program and varying the physical stimulus according to the exercise program; and
a sensor integrated within the insertable device and coupled to the controller, wherein the sensor is configured to measure a reaction time of the muscle contracting in response to the operation of the stimulation mechanism by the controller and wherein the controller is configured to receive feedback from the sensor.

2. The apparatus of claim 1, wherein the feedback from the sensor comprises results of the exercise programs.

3. The apparatus of claim 2, further comprising a display unit coupled to the apparatus on which to view the results of the exercise programs.

4. The apparatus of claim 2, further comprising computer program code for analyzing the exercise program results, and, based on the results, automatically determining a next exercise program appropriate for a user.

5. The apparatus of claim 2, further comprising computer program code for analyzing the exercise program results, and, based on the results, automatically implementing a next exercise program appropriate for a user.

6. The apparatus of claim 2, further comprising an interface to a computer for sending the exercise program results to a user.

7. The apparatus of claim 6, wherein the interface is a wireless interface.

8. The apparatus of claim 1, further comprising a control on the apparatus configured for interaction by a user to activate the exercise programs.

9. The apparatus of claim 1, further comprising a docking station for receiving the apparatus, the docking station electrically coupled to the apparatus for providing power to the apparatus or communicating with the apparatus.

10. The apparatus of claim 1, further comprising an external device for manipulating the controller, the external device communicating remotely with the controller.

11. The apparatus of claim 1, wherein the sensor comprises a pressure sensor.

12. The apparatus of claim 1, wherein the sensor comprises an EMG signal sensor.

13. The apparatus of claim 1, wherein the sensor can perform a calibration before providing feedback to the controller.

14. The apparatus of claim 1, wherein the stimulation mechanism is a motor for vibrating the device.

15. The apparatus of claim 1, further comprising a rechargeable or replaceable power source coupled to and powering the stimulation mechanism.

16. The apparatus of claim 1, wherein the instruction specified by the exercise program indicates a strength of the operation of the stimulation mechanism.

17. The apparatus of claim 1, wherein the instruction specified by the exercise program indicates a duration of the operation of the stimulation mechanism.

18. The apparatus of claim 1, wherein the sensor is configured to measure Kegel muscle contraction activity.

19. A method for exercising the Kegel muscles, the method comprising:
   initiating a first exercise program in an apparatus inserted in a body of a user, wherein an exercise program specifies operation of a stimulation mechanism integrated within the apparatus, the stimulation mechanism configured to deliver one or more physical stimuli to the user at a location of the inserted apparatus, and the operation corresponding with an instruction specified by the exercise program and varying the physical stimulus according to the exercise program;
   monitoring, via a sensor integrated within the apparatus, results of the first exercise program performed by the user on the inserted apparatus, wherein the results comprise a measure of reaction time of the muscle contracting in response to operation of the stimulation mechanism by the controller;
   responsive to the results monitored, selecting a second exercise program in the apparatus customized to the user based on the results of the first exercise; and
   initiating the second exercise program.

20. The method of claim 19, wherein the exercise program results comprise feedback from the sensor coupled to the apparatus.

21. The method of claim 19, the method further comprising providing the exercise program results for display.

22. The method of claim 19, wherein the method of engaging in an exercise program by a user comprises:
   communicating, via the stimulation mechanism, to a user to optionally relax the Kegel muscles to allow the sensor coupled to the apparatus to perform a calibration;
   providing a first physical stimulus to the user signaling to contract the Kegel muscles; and
   providing a second physical stimulus to the user signaling to relax the Kegel muscles.

23. The method of claim 19, the method further comprising:
   after providing a first physical stimulus by the stimulation mechanism during the first exercise program:
      responsive to a muscle contraction having been performed correctly by a user, providing a second stronger physical stimulus by the stimulation mechanism; and
      responsive to a muscle contraction having been performed incorrectly by a user, providing a second weaker physical stimulus by the stimulation mechanism.

24. The method of claim 19, wherein the second exercise program is selected by a method comprising:
   analyzing, via a controller integrated within the apparatus, the results monitored from the first exercise program; and
   selecting a more challenging or less challenging second exercise program, based on the analysis of the results monitored from the first exercise program.

25. A method for exercising the Kegel muscles, the method comprising:
   initiating a first exercise program in an apparatus inserted in a body of a user, wherein an exercise program specifies operation of a stimulation mechanism integrated within the apparatus, the stimulation mechanism configured to deliver one or more physical stimuli to the user at a location of the inserted apparatus, and the operation corresponding with an instruction specified by the exercise program and varying the physical stimulus according to the exercise program;
   monitoring, via a sensor integrated within the apparatus, results of the first exercise program performed by the user on the inserted apparatus, wherein the results comprise a measure of reaction time of the muscle contracting in response to operation of the stimulation mechanism by the controller; and
   initiating a second exercise program, based on the results of the first exercise program, in the apparatus selected by the user.

26. The method of claim 25, wherein the exercise program results comprise feedback from the sensor coupled to the apparatus.

27. The method of claim 25, further comprising providing the exercise program results for display.

28. The method of claim 25, wherein the method of engaging in an exercise program by a user comprises:
   communicating, via the stimulation mechanism, to a user to optionally relax the Kegel muscles to allow the sensor coupled to the apparatus to perform a calibration;
   providing a first physical stimulus to the user signaling to contract the Kegel muscles; and
   providing a second physical stimulus to the user signaling to relax the Kegel muscles.

29. The method of claim 25, the method further comprising:
   after providing a first physical stimulus by the stimulation mechanism during the first exercise program:
      responsive to a muscle contraction having been performed correctly by a user, providing a second stronger physical stimulus by the stimulation mechanism; and
      responsive to a muscle contraction having been performed incorrectly by a user, providing a second weaker physical stimulus by the stimulation mechanism.

30. The method of claim 25, wherein the second exercise program is selected by a method comprising:
   displaying the results of the first exercise program to a user; and
   receiving a selection for a second exercise program by the user.

31. The method of claim 25, wherein the second exercise program is selected by a method comprising:
   analyzing, via a controller integrated within the apparatus, the results monitored from the first exercise program,
   displaying one or more exercise programs to a user, wherein the one or more exercise programs are either more challenging or less challenging than the first exercise program, depending on the analysis of the results monitored from the first exercise program; and receiving a selection for a second exercise program by the user.

\* \* \* \* \*